(12) United States Patent
Guha et al.

(10) Patent No.: US 7,105,848 B2
(45) Date of Patent: Sep. 12, 2006

(54) DUAL LEVEL OUT-OF-FOCUS LIGHT SOURCE FOR AMPLIFICATION OF DEFECTS ON A SURFACE

(75) Inventors: Sujoy Guha, San Diego, CA (US); Terrell Nils Lassiter, San Diego, CA (US)

(73) Assignee: Wintriss Engineering Corporation, San Diego, CA (US)

( * ) Notice: Subject to any disclaimer, the term of this patent is extended or adjusted under 35 U.S.C. 154(b) by 0 days.

(21) Appl. No.: 10/413,699

(22) Filed: Apr. 15, 2003

(65) Prior Publication Data

US 2004/0000652 A1    Jan. 1, 2004

Related U.S. Application Data

(60) Provisional application No. 60/373,230, filed on Apr. 15, 2002.

(51) Int. Cl.
*G01N 21/88* (2006.01)
*G01N 21/86* (2006.01)
*G01V 8/00* (2006.01)

(52) U.S. Cl. .............. 250/559.45; 250/559.4; 356/237.1; 356/239.1

(58) Field of Classification Search ...............
250/559.45–559.46, 559.48, 559.4, 559.42;
356/237.1–237.3, 238.2, 239.1, 429–431
See application file for complete search history.

(56) References Cited

U.S. PATENT DOCUMENTS

| | | | |
|---|---|---|---|
| 4,606,634 A * | 8/1986 | Bieringer | 356/239.4 |
| 5,132,791 A * | 7/1992 | Wertz et al. | 348/88 |
| 5,274,243 A | 12/1993 | Hochgraf | |
| 5,402,228 A | 3/1995 | Jordan et al. | |
| 5,416,594 A | 5/1995 | Gross et al. | |
| 5,471,298 A | 11/1995 | Moriya | |
| 5,526,119 A * | 6/1996 | Blit et al. | 356/402 |
| 5,544,256 A | 8/1996 | Brecher et al. | |
| 5,684,530 A | 11/1997 | White | |
| 5,742,398 A | 4/1998 | Laucoumet | |
| 5,764,874 A | 6/1998 | White | |
| 5,790,247 A | 8/1998 | Henley et al. | |
| 5,835,207 A * | 11/1998 | Sugiura et al. | 356/124 |
| 5,870,204 A | 2/1999 | Chiu et al. | |
| 6,166,393 A | 12/2000 | Paul et al. | |
| 6,297,879 B1 | 10/2001 | Yang et al. | |
| 6,433,867 B1 | 8/2002 | Esquivel | |

* cited by examiner

*Primary Examiner*—Stephone B. Allen
*Assistant Examiner*—Patrick J. Lee

(57) ABSTRACT

A web defect inspection system includes line scan cameras positioned across the width of a web and a dual-level out-of-focus light source for illuminating the web. An illumination surface of the dual-level light source has a bright portion adjacent a dark portion. One such dual-level light source is provided by covering a portion of a diffused light surface with an opaque material having a sharp edge. The pixels of each line scan camera are aligned with the dark to light transition of the light source so that each pixel has a no-defect brightness level equal to half of a relative brightness level of the bright portion of the dual-level light source. An image of a defect-free portion of the web consists of pixels having relative brightness levels within a pre-determined range of the no-defect brightness level. Images of defects on the web surface appear three-dimensional as bright and dark areas. The nature of the defect, that is, whether the defect is concave or convex, is determined based upon the orientation of the dual-level light source and the direction of movement of the web.

24 Claims, 8 Drawing Sheets

1

DUAL LEVEL OUT-OF-FOCUS LIGHT SOURCE FOR AMPLIFICATION OF DEFECTS ON A SURFACE

RELATED APPLICATIONS

This application claims the benefit of priority under 35 U.S.C. 119(e) to provisional U.S. patent application Ser. No. 60/373,230, filed Apr. 15, 2002 which is incorporated herein by reference in its entirety.

FIELD OF THE INVENTION

This invention relates generally to material inspection, and more specifically to the optical amplification of defects on a surface utilizing dual level out-of-focus light source.

BACKGROUND OF THE INVENTION

Manufacturing systems often require surface inspection to detect flaws and contamination that render a product unsuitable for sale. For example, surface inspection systems are utilized to inspect moving webs of materials. A "web" is a flat material produced continuously in large quantities and at very high rates. Typical web material includes fabrics, sheet metal, paper, and non-woven plastic, etc. Inspection of the web material surface is required during production to find flaws and defects. Failure to detect these flaws and defects may result in thousands of feet of unusable web material.

Automated inspection systems of surfaces for defects typically utilize cameras which capture images of the surface under inspection. The images are then evaluated using hardware and/or software to detect defects. Proper illumination of the surface under inspection is essential for acceptable imaging by the cameras. A basic illumination system consists of a bright light source that is distributes uniform light across the surface under inspection. However, this basic illumination results in "flat" or two-dimensional images which may not reveal the presence of defects on the surface. Flat images often highlight dust on the inspected surface resulting in false identification of defects.

The use of multiple light sources which are directed at the surface enhances the visual appearance of materials that are under inspection. For example, multiple light sources may be positioned to illuminate the surface from various angles. The light sources may utilized varying wavelengths of light to enhance surface features. Some systems strobe or sequentially switch lights to enhance camera images. Defects which cannot be seen with uniform illumination become visible when utilizing these types of illumination schemes.

The above-described illumination systems present disadvantages of use in a surface inspection system. Flat illumination does not provide sufficient lighting for a camera to detect small defects. Because flat illumination highlights dust on the surface, this type of illumination may not be suitable for harsh environments. The use of multiple light sources increases the cost of a defect detection system as well as the cost for operation of the system. Strobe or switched lights require switching and control hardware which increases cost and complexity of the system. In addition, the existing illumination systems limit the resolution of the defect detection. Therefore, a need continues to exist for an illumination source for use in a defect detection system that allows a camera to produce images of easily-identifiable defects.

SUMMARY OF THE INVENTION

It is an object of the present invention to provide a single, dual level light source that illuminates a material under inspection such that a camera can produce enhanced images of defects.

It is also an object of the present invention to provide a defect detection system which produces images of surface defects that appear three dimensional in the image.

It is another advantage to provide a two-tone light source that results in an image provides differentiation between a convex defect and a concave defect.

Another advantage of the present invention is to provide an defect detection system that may be adjusted easily to detect defects of a desired size.

Yet another advantage is to provide an defect detection system which can be used in dusty environments without false identification of surface defects.

In an exemplary embodiment of the present invention, a single dual level out-of-focus light source provides lines scan cameras with illumination that allows each camera to produce enhanced images of defects on a surface under inspection, such as a web. Defects which cannot be seen in images illuminated with uniform lighting become visible when utilizing the dual level out-of-focus light source. The exemplary dual level light source includes light emitting elements covered by a diffuser to evenly distribute light rays. A portion of the diffuser, is covered by an opaque material having a straight sharp edge that does not allow light rays to escape the covered portion of the diffuser. The single row of pixels of each line scan camera are aligned with the dual level light source by positioning a center line of the pixels with the straight edge of the opaque material. If the pixels are properly aligned with the light source, and the camera has a narrow depth of field which does not include the light source, an out-of-focus light source image, which varies abruptly from the full brightness of the illumination source to black, is "seen" by each pixel of the camera. In the exemplary embodiment, a relative brightness level of each aligned pixel is one half the maximum brightness of the light emitting portion of the light source.

A range of brightness is established in the exemplary embodiment by defining the dark portion of the light source as having a brightness level of 0, and the bright portion of the light source as having a brightness level of 256. This range may be narrowed to a maximum of 250, for example, to avoid light saturation conditions in the camera. This range is utilized to establish a relative brightness scale when a surface under inspection, such as a web, is illuminated for imaging by the line scan cameras.

A material under inspection may be categorized as either opaque or non-opaque. Opaque materials, such as sheet metal, must be illuminated using a light source positioned above the opaque material. Light rays from the light source reflect off of the material surface allowing the camera to capture images of the material surface. Non-opaque or transparent materials, such as film, must be illuminated using a light source positioned behind the material, so that the material is between the light source and the camera. Light rays from the light source are refracted through the back-lit material. The brightness level of each pixel image of the surface illuminated by refracted and reflected light decreases in comparison to the brightness of the light observed by the camera when the material is not present. Thus, in the exemplary embodiment of the invention, the gain of the camera is increased so that a pixel image of the material without a defect has a relative brightness level of approximately one half of a relative maximum brightness. For example, if a range of 0–250 is utilized, then a no-defect relative brightness is defined as 125. A pre-selected range or threshold, e.g., 100–150, then may be used to identify acceptable pixel brightness for a no-defect condition.

A defect may be categorized as convex or concave, or a combination of the two. On a no-defect surface, the surface and a line perpendicular to the surface are used a references to define the angles of refraction and reflection of the light rays. A defect presents upward and downward sloping surfaces which cause the angles of refraction and reflection to vary. In the exemplary embodiment, the camera pixels are aligned with the opaque edge, as discussed above, so that each pixel of an image of a no-defect surface area has a relative brightness of half of a pre-determined relative maximum brightness. As the defects move into a "sight" line of the pixels, a pixel-size area of the light rays from the light source appear to shift as viewed by the camera. The shift moves the pixel size area into one of the dark portion or the light portion of the surface of the light source depending upon whether the surface of the defect is sloping upwards or downwards at a given position being imaged by the camera.

For example, in a first orientation of the light source surface and a direction of movement of the web wherein the web moves over the light source from dark to bright, an upward sloping surface of a convex or concave defect produces a light area in an image of the defect, and a downward sloping surface of a convex or concave defect produces a dark area in the image. Thus, a convex defect appears as a light to dark area, and a concave defect appears as a dark to light area. Due to the light to dark, and dark to light, transitions of the image, the defect appears to be three-dimensional.

The desired size of defect detection, that is, the sensitivity of the defect detection system, is controlled by adjusting the depth of field of the line scan cameras. A shallow depth of field requires a larger out-of-focus pixel size area of the light source surface to provide the illumination for an in-focus pixel size area of the material under inspection. The shallow depth of field image detects relatively large defects, and the surface features of the material do not appear in an image of the material. As the depth of field increases, the out-of-focus pixel size area of the light source becomes smaller, such that smaller defects are detectable. In addition, the surface features of the material become prominent in an image of the material. The sensitivity of the defect detection system must be chosen so that defects are detectable without the surface features of the material overwhelming the image.

BRIEF DESCRIPTION OF THE DRAWINGS

The present invention will be better understood from the accompanying drawings in which.

DESCRIPTION OF THE PREFERRED EMBODIMENT

Figure 1:
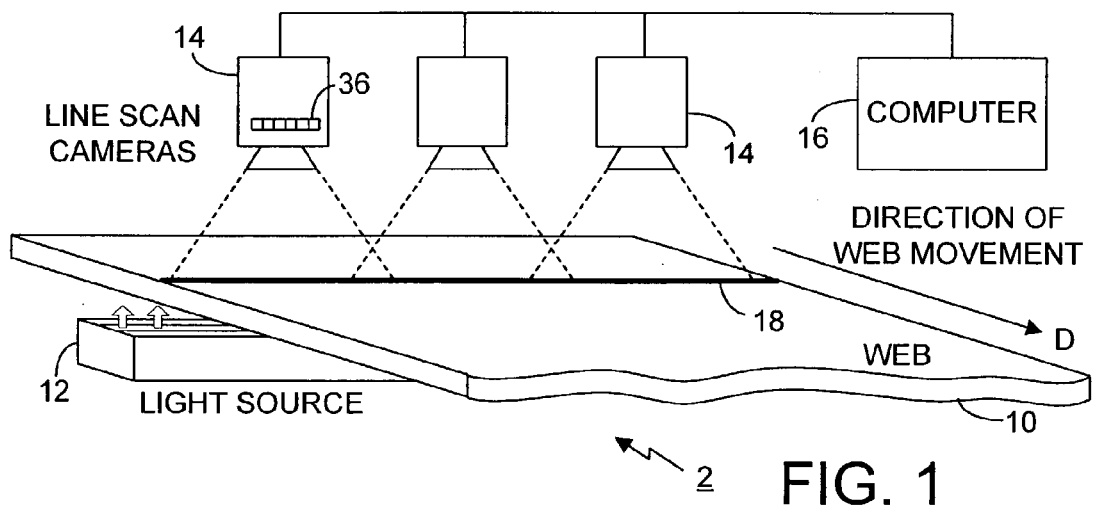
FIG. 1 is an illustration of a web inspection system utilizing line scan cameras and a dual level light source of a preferred embodiment of the invention.

FIG. 1 illustrates a web inspection system 2 of a preferred embodiment of the present invention. The web inspection system 2 includes a web material 10 moving in a direction D, a light source 12 for illuminating the web 10. Each fixed line scan camera 14 images a single row of pixels 36 on a portion of the width of the web 10. The combination of fixed line scan cameras 14 inspects a pixel-width line 18 across the width of the web 10. The movement of the web 10 in direction D, allows the entire lengthwise surface of the web 10 to be inspected for defects. The line scan cameras 14 communicate images of the web 10 to a computer 16 for defect analysis. In a preferred embodiment of the invention, the camera performs an analysis on the images of the web 10, and communicates only defect images to the computer 16.

Figure 10:
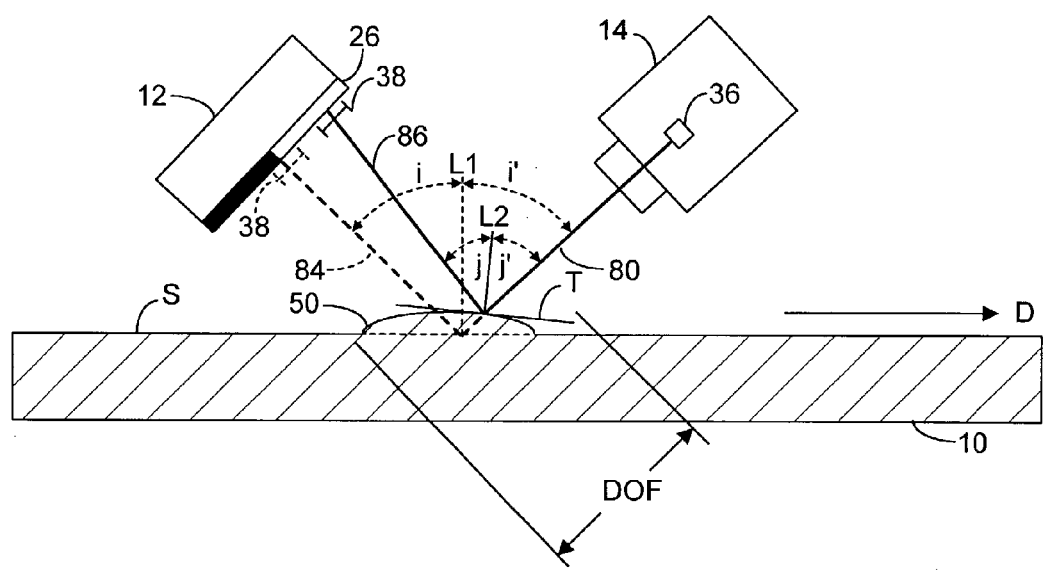
FIG. 10 is an illustration of a front lit surface inspection system utilizing fixed line-scan cameras, a dual-level out-of-focus light source of the preferred embodiment, and an opaque moving material under inspection having a convex defect.
Figure 11:
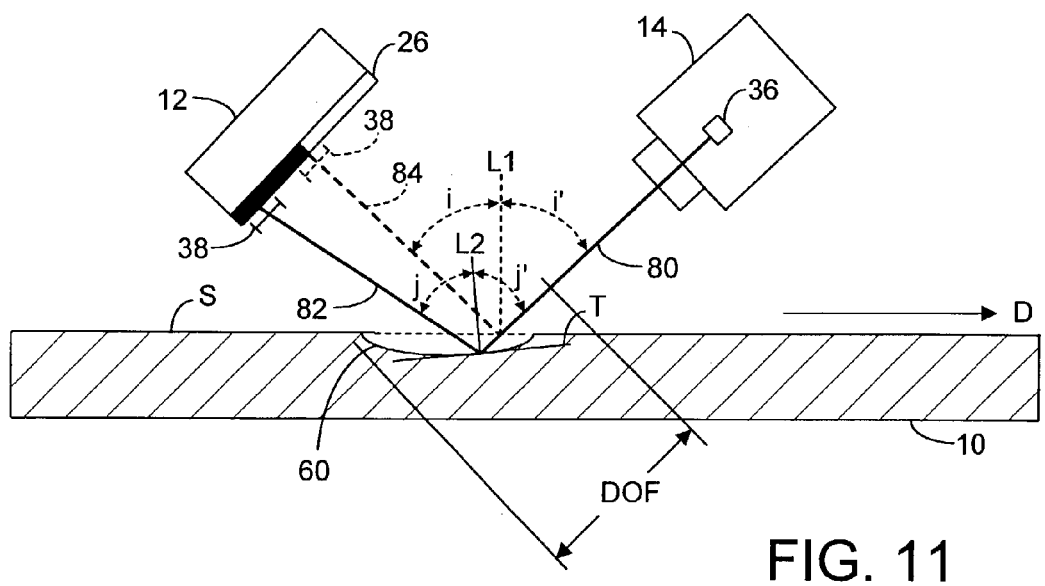
FIG. 11 is an illustration of a front lit surface inspection system utilizing fixed line-scan cameras, a dual-level out-of-focus light source of the preferred embodiment, and an opaque moving material under inspection having a concave defect.

The light source 12 illustrated in FIG. 1 is used to back light a web 10 when the web 10 is a non-opaque material. Light rays from the light source 12 are refracted through the web material 10. In an embodiment of the invention for inspecting opaque material, the web 10 is illuminated utilizing a light that is positioned above the web 10. In a front light embodiment, as illustrated in FIGS. 10 and 11, the light from the light source 12 reflects off of the web 10.

Figure 2:
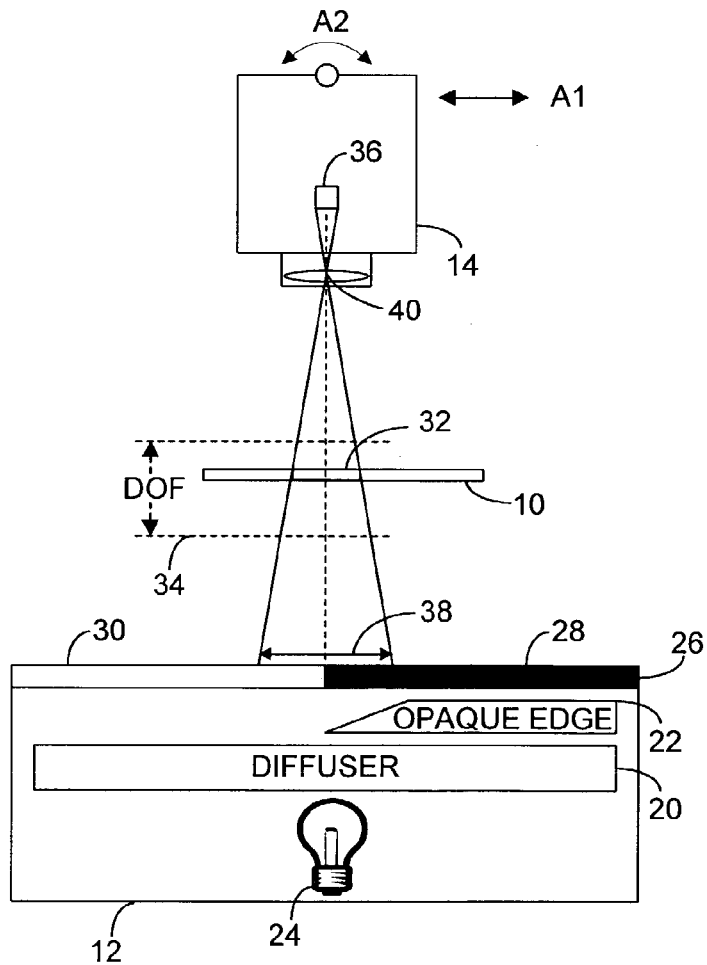
FIG. 2 is an illustration of a dual level light source of the preferred embodiment that is outside of a depth of field of a camera.

FIG. 2 illustrates a dual level light source 12 of a preferred embodiment of the invention. The dual level light source 12 includes light emitting elements 24 such as flourescent lights or light emitting diodes (LEDS), a diffuser 20 placed over the light emitting elements 24, and an opaque edge 22 that covers a portion of the diffuser 20. The diffuser 20 may be tinted to allow specific wavelengths of light rays to be emitted from the light source 12. Similarly, the light emitting elements 24 may be selected to emit specific wavelengths of light. The light source 12 is sufficiently long to ensure even illumination across the width of the web 10. The opaque edge 22 blocks the light rays emanating from a portion of the diffuser 20. This configuration produces a light source 12 that has a dual level light surface 26, that is, a portion of the surface is bright 30, and a portion of the surface is dark 28. The opaque edge 22 of the preferred embodiment is placed on the diffuser 22 such that it covers approximately one half of the diffuser 20. However, the exact placement of the opaque edge 22 is not critical, as it is only necessary that each of the bright portion 30 and the dark portion 28 of the light source surface 26 has a width of at least a pixel 38 as seen by the camera at any given aperture setting. Although FIG. 2 illustrates a preferred embodiment of a dual level light source, any dual level light source 12 that provides a light surface 26 having a bright portion 30 and a dark portion 28 may be utilized to detect defects on a surface 10 in the preferred embodiment of the present invention.

FIG. 2 is a side view of a line scan camera 14 and light source 12 of FIG. 1. Pixel 36 is a digital image of a pixel-size area 32 on a surface 10. A typical line scan camera utilized in a preferred embodiment may include up to 5000 pixels aligned in a direction across a portion of the width of the web 10. The side view of FIG. 2 illustrates one pixel 36 of the total number of pixels. The camera lens 40 is focused on the surface 10, and the depth-of-field (DOF) 34 is set to include the surface 10 but not the light source 12. The depth-of-field defines the area of sharp focus in front of and/or behind the main subject, e.g., the surface 10. The depth-of-field 34 for a fixed camera 14 is set by the f-stop, that is, by opening or closing the camera aperture. As the aperture opening is decreased, the depth-of-field increases. Because the depth-of-field does not include the light source 12, the light source 12 appears out-of-focus to the camera 14. Thus, the light source 12 of the preferred embodiment of the present invention is a dual level, i.e, bright and dark, out-of-focus light source 12.

Continuing with FIG. 2, a pixel-sized area 38 on the surface 26 of the light source 12 is half bright 30 and half dark 28 when the camera pixel 36 is centered on the transition edge between the bright and dark portions 28, 30 of the surface 26 of the light source 12. The brightness of the bright portion 30 of the light source 12 can be measured on an arbitrary brightness scale ranging form 0 to 256. The brightness b of a pixel 36, as sensed by the camera 14, has a brightness level based upon the brightness scale. The brightness level of the pixel 36 varies depending upon the amount of light refracted or reflected from the material surface 10. In other embodiments of the invention, the brightness factor may be set to any preferred range. In the preferred embodiment, to avoid saturation conditions, the brightness level is limited to a range of 0 to 250. The brightness of pixel 36, with surface 10 removed, is 125 since half of the pixel has a brightness of 250, and the half of the pixel has a brightness of 0.

Figure 3A:
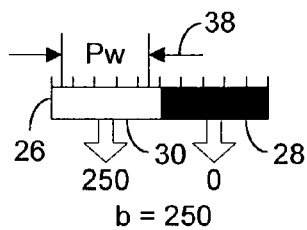
FIG. 3A illustrates a maximum brightness level of a pixel-sized area on the surface of a dual level light source as seen by a camera pixel, wherein the pixel-size area is entirely within a bright portion of the light source surface.
Figure 3B:
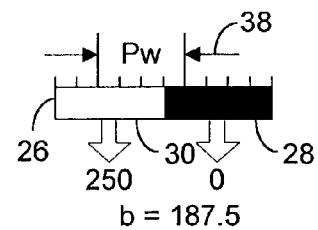
FIG. 3B illustrates a brightness level of a pixel image of a pixel-size area having a greater portion of its area within a bright portion of the light source surface and a lesser portion of its area within a dark portion of the light source surface.
Figure 3C:
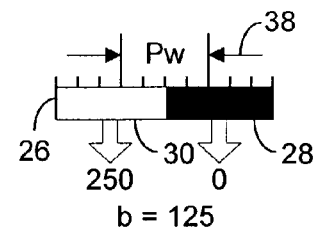
FIG. 3C illustrates a brightness level of a pixel image of a pixel-size area centered halfway within the dark and bright portions of the light source surface.
Figure 3D:
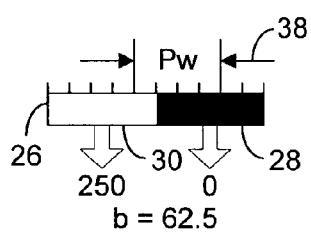
FIG. 3D illustrates a brightness level of a pixel image of a pixel-size area having a greater portion of its area within a dark portion of the light source surface and a lesser portion of its area within a bright portion of the light source surface.
Figure 3E:
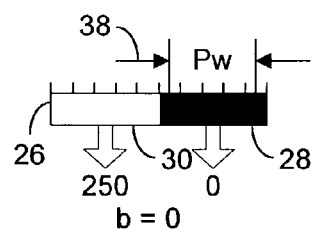
FIG. 3E illustrates a minimum brightness level of a pixel having a width entirely within a dark portion of the light source.

FIGS. 3A–3E illustrate different brightness levels for a pixel 36 imaging a pixel width area 38, Pw, on the surface of a light source 26. FIG. 3A illustrates a maximum brightness level, b=250, of a pixel 36 when the pixel width area Pw 38 is entirely within a bright portion 30 of the light source surface 26. FIG. 3B illustrates a brightness level b=187.5 for a pixel 36 when a fourth of the pixel width area Pw is in the dark portion 28 of the light source surface 26. FIG. 3C illustrates a brightness factor of half of the maximum level, or b=125, when the pixel width area Pw is center between the dark and light portions 28, 30 of the light source surface 26. FIG. 3D illustrates a brightness level b=62.5 for a pixel 36 when a fourth of the pixel width area Pw is in the light portion 30 of the light source surface 26. Similarly, FIG. 3E illustrates a minimum brightness level, b–0, of a pixel 36 when the pixel width area Pw 38 is entirely within a dark portion 28 of the light source surface 26.

Figure 16:
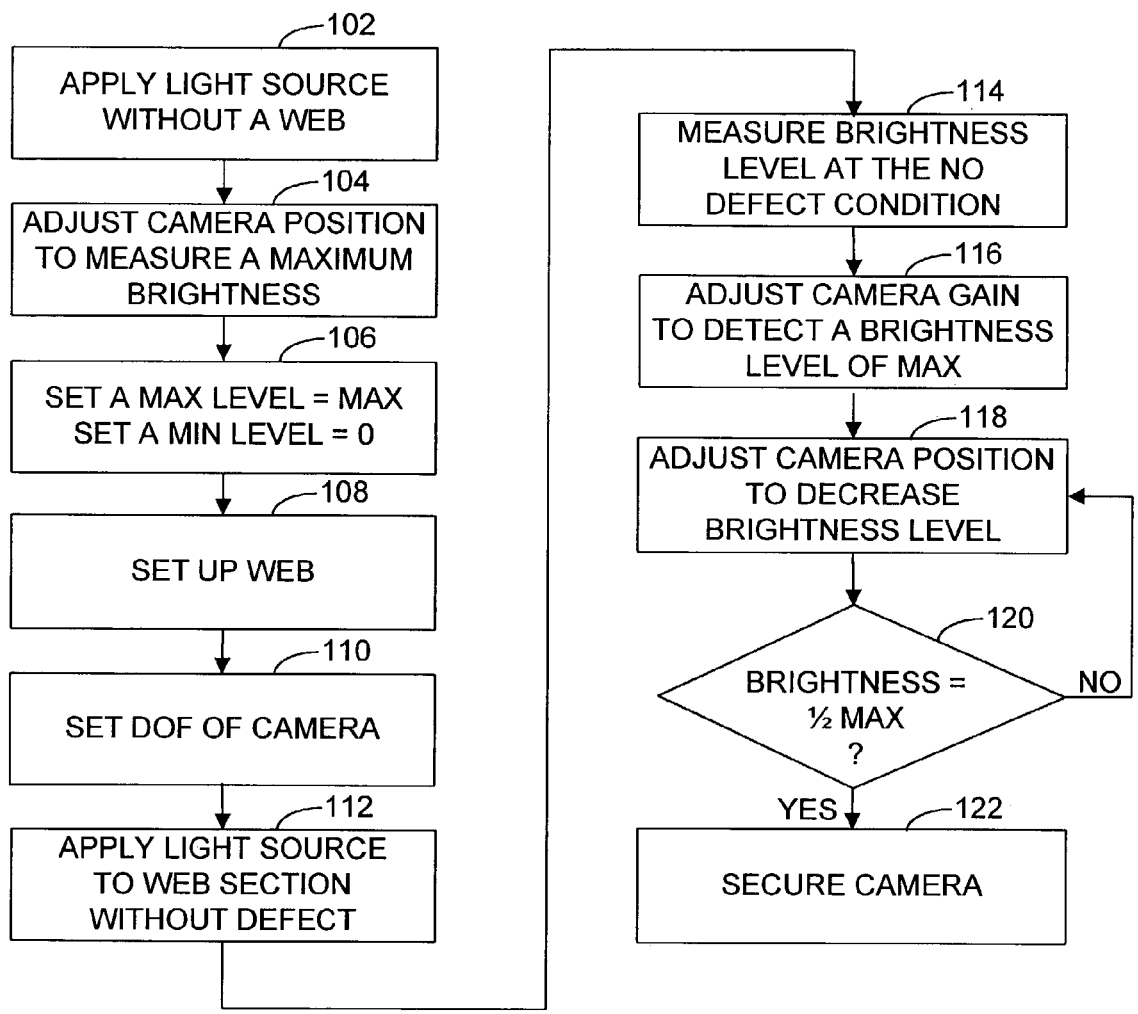
FIG. 16 is a flow diagram for adjusting the camera position with respect to the light source of a preferred embodiment, and for setting the camera gain.

Referring to FIGS. 2 and 16, the camera 14 of the preferred embodiment of the invention is aligned in directions A1 and/or A2 until the pixel 36 has a brightness level of half of a maximum brightness, that is, the center of pixel 36 is centered on the transitional edge between the dark and light portions 28, 30 of the light source surface 26. FIG. 16 is a flow diagram of a preferred method for setting the camera position and brightness level for a pixel 36. In step 102, the light source 12 is applied without a web 10. The camera position is adjusted to measure a maximum brightness, step 104. The maximum brightness is assigned an arbitrary maximum level factor of "max", e.g., b=250, in step 106. A minimum brightness level is set to b=0. In steps 108 and 110, the web 10 is positioned between the light source 12 and the camera 14, and the depth of field 34 is set to include the web surface 10 but not the light source 12. The light source 12 is applied to a section of the web 10 that is known to have no defects, in step 112.

The brightness of pixel 36 is measured at the no defect condition, step 114. Because the presence of the web 10 reduces the amount of light detected by the camera 14, the brightness level of the pixel 36 is reduced by a percentage from the maximum level of brightness when the web 10 is not present. Thus, the gain of the camera is adjusted in step 116 until the detected brightness is equal, for example, to the maximum level. However, another arbitrary maximum level and a threshold may be established at this step. Once the camera gain is increased, the camera position is adjusted appropriately in steps 118 and 120, e.g., in directions A1 and A2, until the brightness level is half of the maximum brightness level. The camera 14 is secured in step 122 once the brightness is half of the maximum brightness level. The secured position ensures that the camera pixel 36 is centered evenly on the bright and dark portions 30, 28 of the light source surface 26 for a no defect condition of the web 10.

FIG. 10 illustrates one method of setting the position of the camera 14 with respect to the light source 12. The steps of this method may be reordered as long as camera 14 is properly positioned to establish a brightness scale and a no-defect parameter condition. Also, alternate embodiments may be employed to establish no defect parameters for the camera 14, light source 12 and web 10. For example, in one alternate embodiment, a light source 12 without an opaque edge is utilized to apply illumination to a web. The camera is focused on a portion of the web 10 without a defect, the DOF 34 is set, and the gain of the camera is increased until the pixel 36 detects a desired maximum brightness level. The opaque edge 22 is slid over the light source 12 until the brightness level is one half the relative maximum brightness. A one half brightness level indicates that the pixel 36 is imaging one half of the bright portion 30 of the light source 12 and one half of the dark portion 28 of the light source 12. Finally, the opaque edge 22 is secured. In a preferred embodiment, it is desirable to provide a single unit light source 12 which already includes the opaque edge 22. Thus, methods for centering the pixel 36 on the light source 12 must be employed as opposed to alternate methods for centering the opaque edge 22 within the pixel 36.

Figure 4:
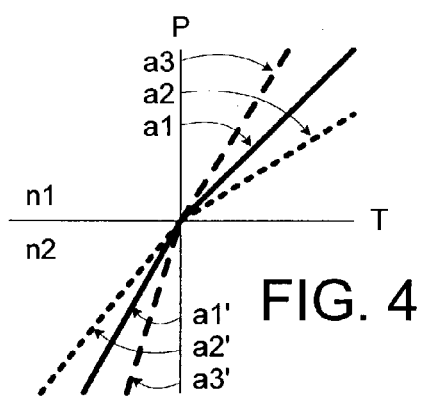
FIG. 4 illustrates refraction of light at a surface T.

Inspection of non-opaque web material 10 typically utilizes back lighting, that is, the web 10 is located between the light source 12 and the camera 14. As shown in FIG. 4, the web material 10 refracts the light emitted from the light source 12 according to Snell's law, which is defined as $$n1 \times \cos(a1) = n2 \times \cos(a1').$$  Equation 1

Figure 5:
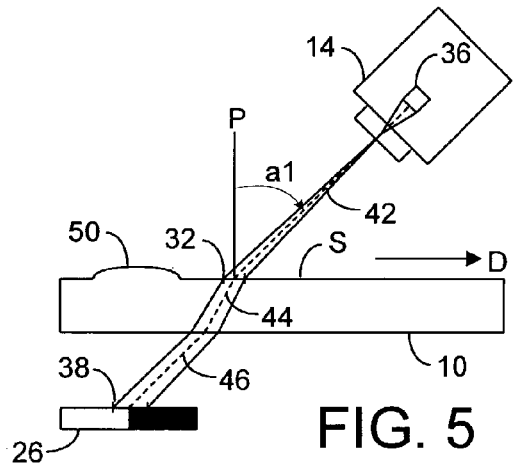
FIG. 5 illustrates a line scan camera observing a pixel width of a web surface having no defect, wherein the web surface is lit using a back light.
Figure 6:
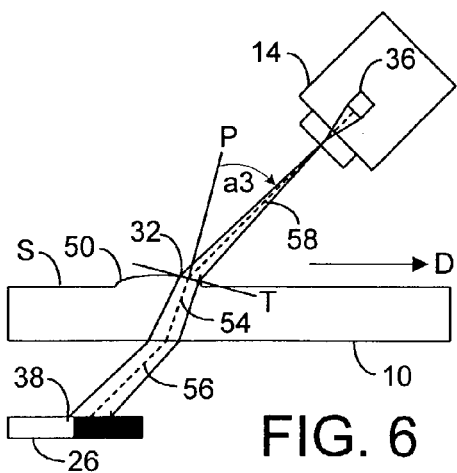
FIG. 6 illustrates a line scan camera imaging a pixel size area of a web surface having a defect with an upward sloping surface, wherein the web surface is illuminated using a back light.
Figure 7:
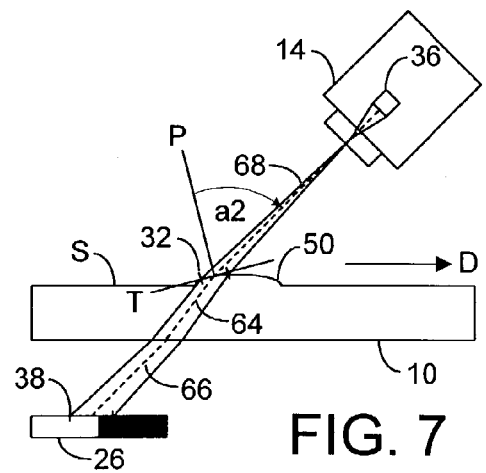
FIG. 7 illustrates a line scan camera imaging a pixel size area of a web surface having a defect with a downward sloping surface, wherein the web surface is illuminated using a back light.

Angle a1 is measure with respect to a line P perpendicular to a tangent line T. As angle a1 increase to angle a2, angle a1' increase to angle a2'. As angle a1 decreases to angle a3, angle a1' decreases to angle a3' according to equation 1. FIGS. 5–7 illustrate the applicability of Snell's law to the present invention.

FIG. 5 illustrates a single pixel 36 image for a no-defect web 10 condition. The camera 14 is shown at an angle to clearly show the light refraction in the web material 10. The camera 14 is focused on the surface S of a web 10 moving in direction D. The position of the web 10 in FIG. 5 illustrates a no-defect position. A defect 50 is shown approaching the "line of sight" 42 of the camera 14. The pixel 36 receives light rays 46, 44, 42 from a pixel size area 38 that is centered on the light source surface 26 for the no-defect condition. The dotted line 46, 44, 42 indicates the center line of the light rays of the pixel size area 38, and the solid lines represent the light rays at the edges of the pixel size area 38. Light rays 46 emitted from the light source 26 are refracted at the bottom surface of the web. The light rays in the web 44 are refracted again on the top surface of the web 10, where angle a1 is measured from a line P perpendicular to the surface S of the web 10. An in-focus pixel-size area 32 on the surface of the web 10 receives light rays from a larger out-of-focus pixel-size area 38 on the surface of the light source 26. For example, a pixel-size area 32 that is 2 mils in width on the surface of the web 10, may be 200 mils in width on the light source surface 26.

FIG. 6 illustrates a decrease in the brightness of pixel 36 when a defect 50 is encountered on the web 10. Referring also to FIG. 4, the light rays are refracted at an upward sloping surface of the defect 50, as seen by the camera 14, which is represented as a tangent plane T. Angle a3 is measured from a line P perpendicular to tangent plane T, and is less than angle a1 of FIG. 5. The decrease of angle a1 to angle a3 shifts the pixel size area 38 of light rays 56, 54, 58 received by the camera 14 towards the dark portion of the light source surface 26. Therefore, the relative brightness level of pixel 36 decreases. FIG. 7 illustrates a subsequent position of the defect 50 as the web 10 continues in direction D. The downward sloping surface of the defect 50, represented by tangent line T, increases angle a1 to angle a2, and shifts the pixel size area 38 of light rays 66, 64, 68 received by the camera 14 towards the bright portion of the light source surface 26. Therefore, the relative brightness level of pixel 36 increases.

The defect detection system shown in FIGS. 5–7, produces images of convex defects, such as bumps on the surface of the web 10, that appear as dark areas followed by bright areas since the upward slopes of the defect 50 are followed by the downward slopes of the defect 50. Concave defects (not shown), such as dents in the surface of the web 10, appear as bright areas followed by dark areas since the downward slopes of the concave defects are followed by the upward slopes. The defect images of bright to dark areas, or dark to bright areas depend upon the direction D of movement of the web 10, the orientation of the bright and dark portions of the light source surface 26, and whether the defect is convex or concave.

Figure 8:
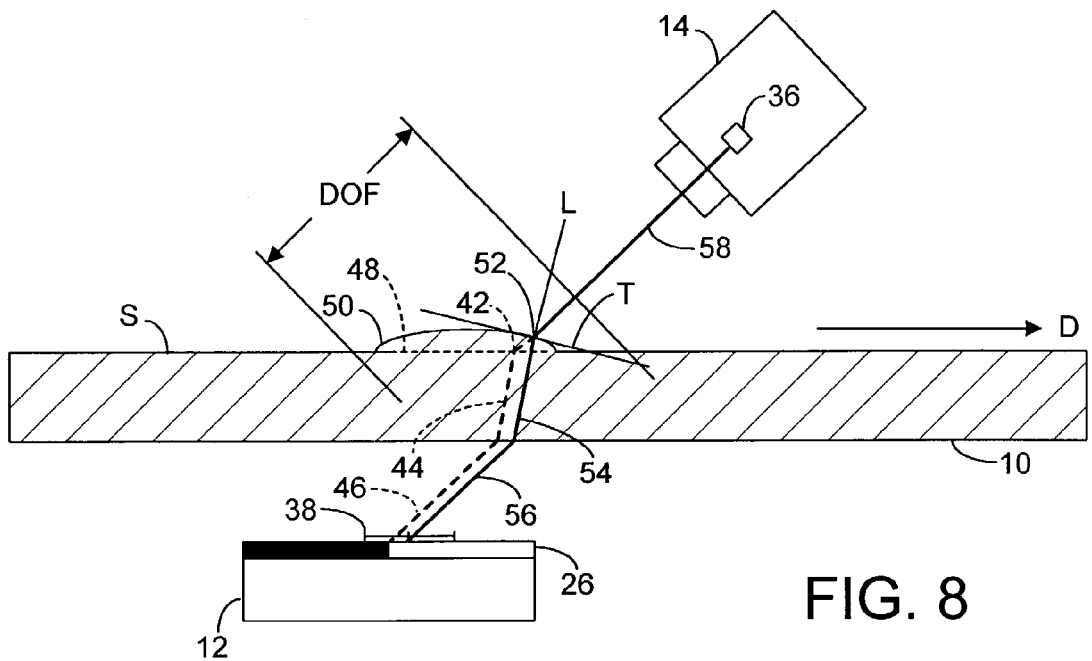
FIG. 8 is an illustration of a back-lit surface inspection system utilizing fixed line-scan cameras, a dual-level out-of-focus light source of the preferred embodiment, and a non-opaque moving material under inspection having a convex defect.
Figure 9:
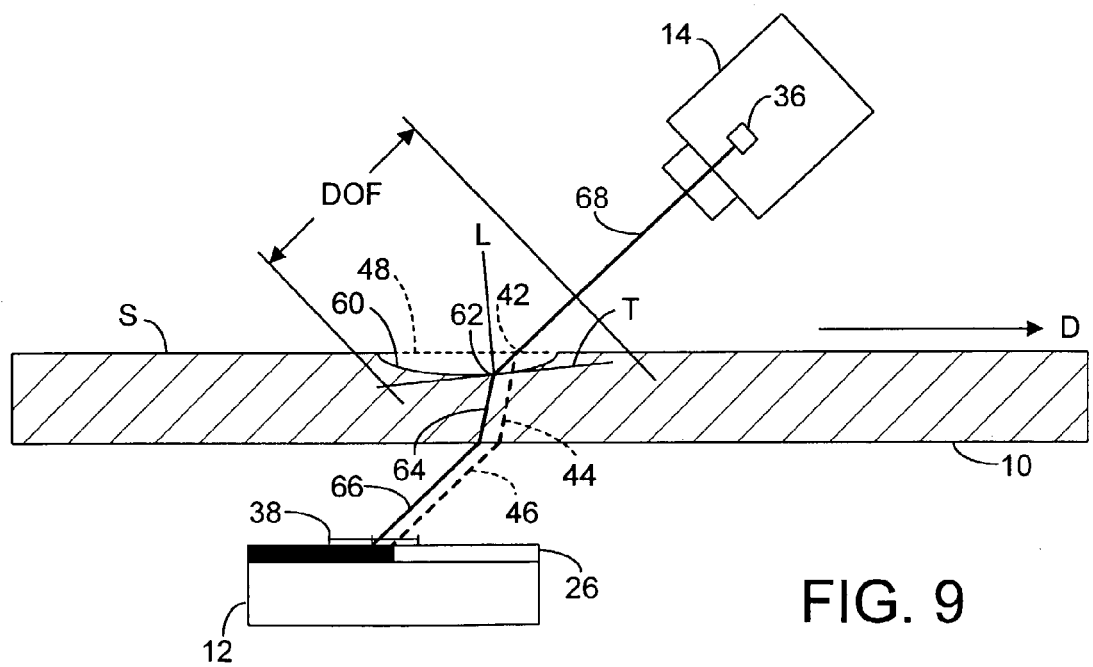
FIG. 9 is an illustration of a back lit surface inspection system utilizing fixed line-scan cameras, a dual-level out-of-focus light source of the preferred embodiment, and a non-opaque moving material under inspection having a concave defect.

FIG. 8 is an illustration of a back-lit surface inspection system utilizing fixed line-scan cameras 14, a dual-level out-of-focus light source 12 of the preferred embodiment, and a non-opaque moving material 10 under inspection having a convex defect 50. FIGS. 8–10 illustrate the center light rays, only, that are detected by the camera 14 for the pixel image 36. However, the width of the pixel-size areas 38 on the surface 26 of the light source 12 are illustrated to show the relative brightness level of the pixel 36. The bright and dark portions of the light source surface 26 are reversed from those of the light source surface illustrated in FIGS. 5–7.

Continuing with FIG. 8, a depth-of-field DOF of the camera is set to include the surface S of a web 10 and to exclude the surface 26 of a dual-level light source 12 such that the surface 26 of the light source 12 remains out-of-focus to the camera 14. Light rays 46, 44, 42 from a pixel-size area (not shown) that is centered on the light source surface 26 are refracted through a web material 10 of a no defect surface 48, shown as a dotted line, resulting in a brightness level of pixel 36 that is one half of a relative maximum brightness. As the defect moves into the pixel-width "sight line" 58 of the camera 14, the relative brightness of pixel 36 increases or decreases depending upon the angle of incidence of the pixel-width refracted light rays 58 measured with respect to a line L perpendicular to a tangent line T. The rising edge of the defect 50 shifts the detected light rays emanating from the pixel-size area 38 towards the bright portion of the light source surface 26. Thus, a convex defect 50 appears on an image of the web 10 as a bright area followed by a dark area.

FIG. 9 is an illustration of a back-lit surface inspection system utilizing fixed line-scan cameras 14, a dual-level out-of-focus light source 12 of the preferred embodiment, and a non-opaque web 10 moving in direction D having a concave defect 60. The pixel width light ray path 46, 44, 42 is shown (dotted lines) for a no defect condition. The brightness level of pixel 36 for the no defect condition is half of a relative maximum brightness level. The downward sloping surface of the concave defect 60, as seen by the camera 14, shifts the detected light rays emanating from the pixel-size area 38 towards the dark portion of the light source surface 26. Therefore, a concave defect 60 appears on an image of the web 10 as a dark area followed by a light area.

Figure 13:
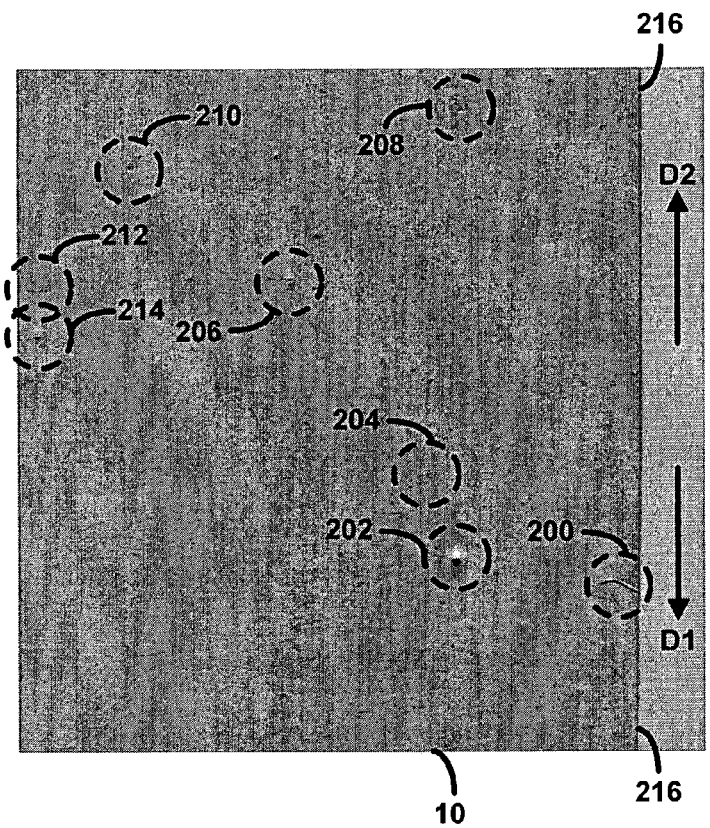
FIG. 13 is an image of the same defects as shown in FIG. 11 utilizing a dual level out-of-focus light source of the preferred embodiment, wherein the depth-of-field of the camera is at a minimum setting, i.e., the lens aperture is open at an f-stop of 2.8.
Figure 14:
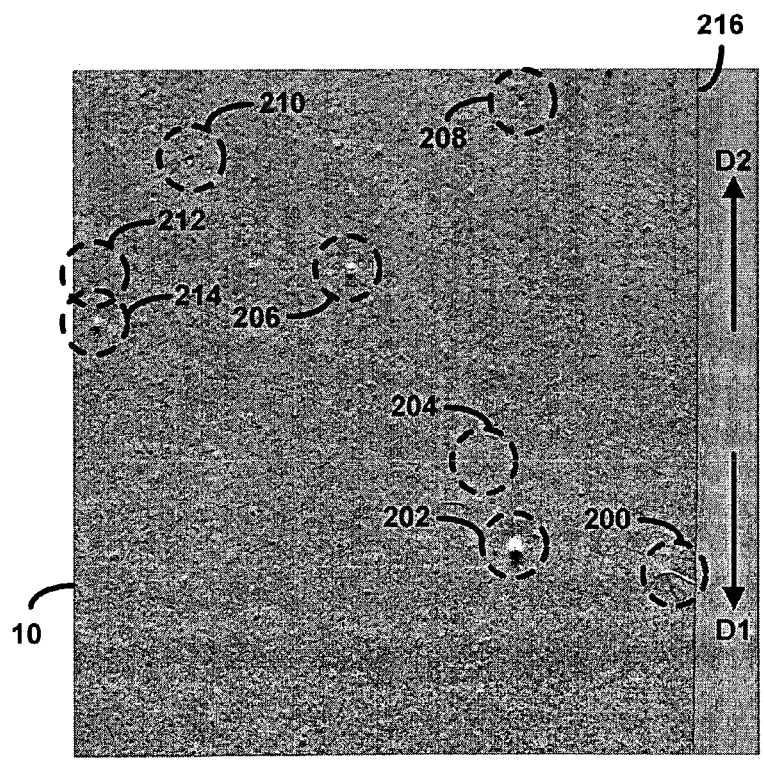
FIG. 14 is an image of the same defects as shown in FIG. 11 utilizing a dual level out-of-focus light source of the preferred embodiment, wherein the depth-of-field of the camera is at a second setting with the lens aperture at an f-stop of 8.
Figure 15:
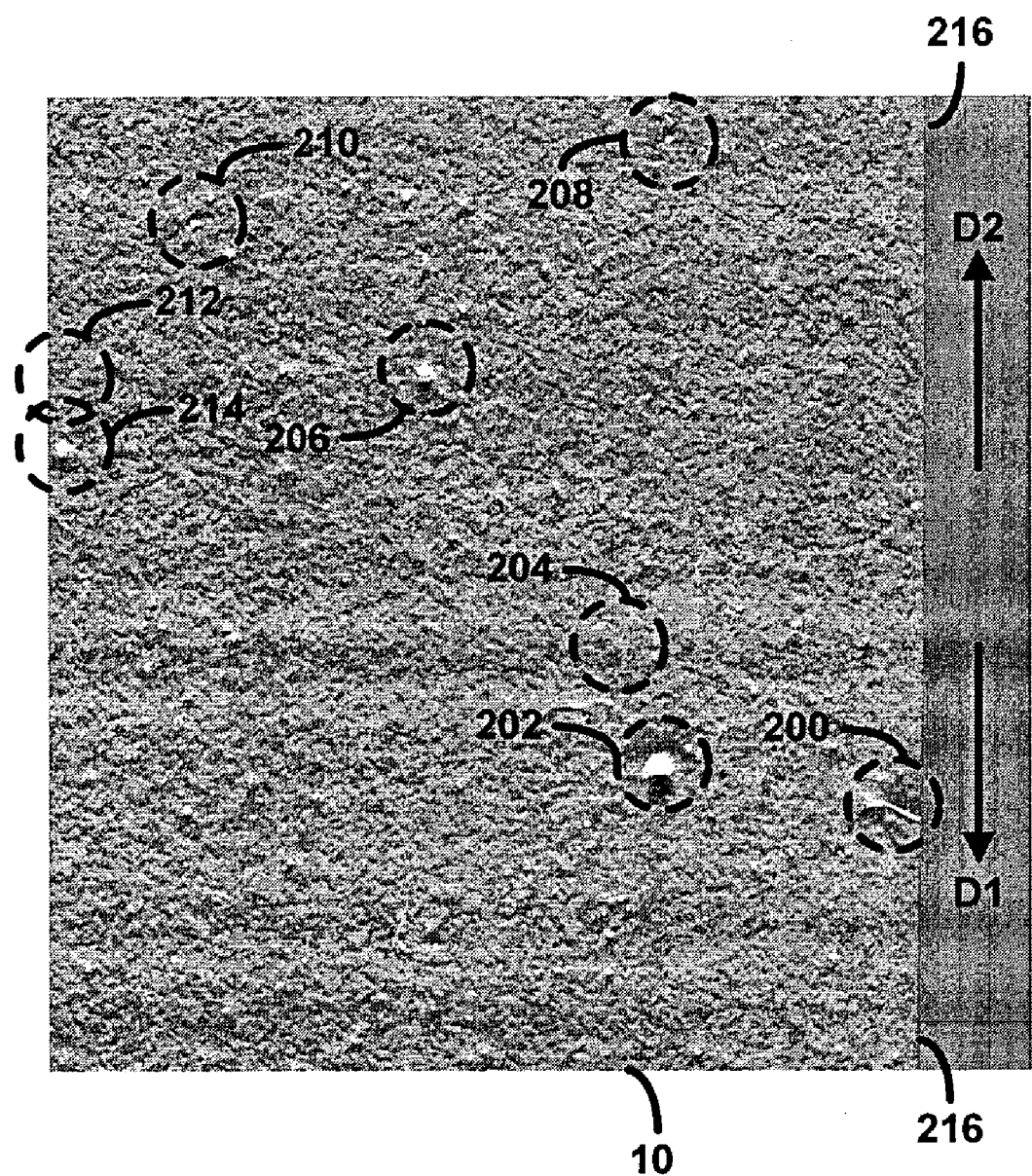
FIG. 15 is an image of the same defects as shown in FIG. 11 utilizing a dual level out-of-focus light source of the preferred embodiment, wherein the depth-of-field of the camera is at a maximum setting, i.e., the lens aperture is at an f-stop of 16.

Defect 202 of the images of FIGS. 13–15 is a convex defect for a surface inspection system configured according to the system shown in FIGS. 8 and 9, where D2 is the direction of the web movement. As shown in FIGS. 13–15, defect 202, which appears as a bright area followed by a dark area, is a convex defect. Defect 210, which appears as a dark area followed by a light area, is a concave defect. As noted above, if the direction of the web is reversed to the direction D1, then bright to dark image areas would indicate the presence of concave defects, and dark to bright areas would indicate the presence of convex defects. Also as noted above, reversing the dark and light portions of the light source 12 will define the type of defect for a given direction D1 or D2.

FIGS. 10 and 11 illustrate a front lit surface inspection system utilizing fixed line-scan cameras 14, a dual-level out-of-focus light source 12 and an opaque web 10 moving in direction D. An opaque surface S reflects light rays 82, 84, 86. The angle of incidence i, j of light rays 82, 84, 86 with respect to a line L1, L2 perpendicular to a tangent line S, T is equal to the angle of reflection i', j' of the light rays. For a no defect condition, illustrated by dotted lines, the pixel 36 has a relative brightness level of one half of a relative maximum brightness level since the pixel-size area 38 on the surface 26 of the light source 12 is centered on the bright to dark transition of the surface 26. A rising edge of a convex defect 50, as shown in FIG. 10, changes the angles of incidence and reflection j, j' such that the detected light rays emitted from the pixel-size area 38 shift towards the bright portion of the light surface 26. Similarly, a rising surface of a concave defect (not shown) increases the brightness level of the pixel 36. In the system illustrated in FIGS. 10 and 11, a convex defect 50 appears in an image produced by the camera 14 as a bright area followed by a dark area.

FIG. 11 is an illustration of the front lit surface inspection system of FIG. 10 wherein the web 10 includes a concave defect 60. The downward sloping surface of the concave defect 60 appears to the camera to shift the pixel-size area 38 detected by pixel 36 into the darker portion of the light source surface 26. A rising surface of the concave defect 60 appears to shift the pixel-size area 38 into the brighter portion of the light source. Thus, in the system illustrated in FIGS. 10 and 11, a concave defect 60 appears in an image produced by the camera 14 as a dark area followed by a bright area. As noted in the description of the back-lit system of FIGS. 8 and 9, the image of convex and concave defects 50, 60 is dependent upon the orientation of the light source 12 and the direction D of the movement of the web 10 under inspection.

Figure 12:
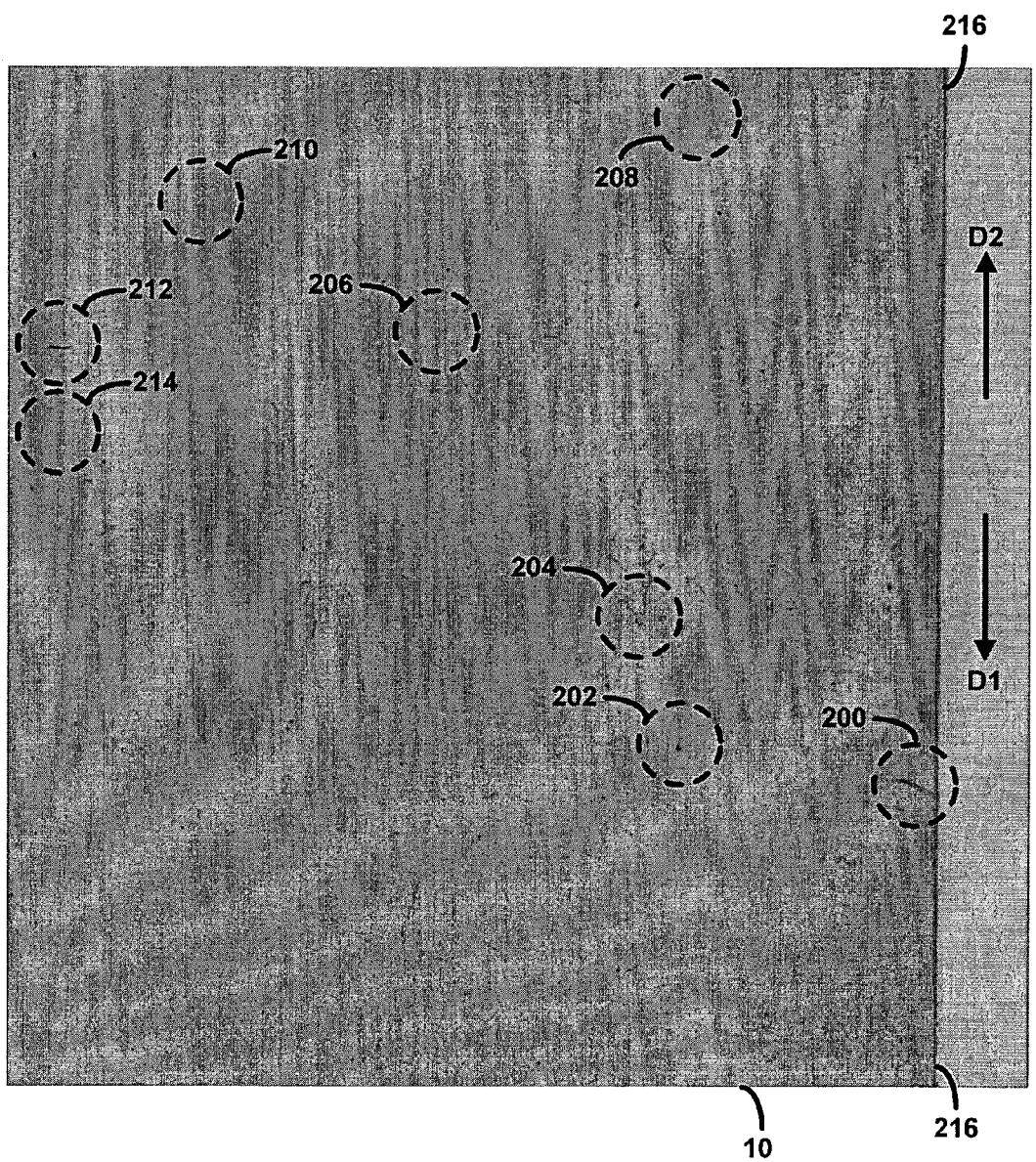
FIG. 12 is a line scan camera image of defects on a sample of non-opaque film utilizing uniform back lighting of the prior art.

FIG. 12 is an image of a non-opaque film 10 utilizing back lighting, which was developed with a line-scan camera 14 and uniform lighting of the prior art. The web edge 216 appears on the right portion of the image. Circled areas 206, 208, 210 and 214 of the web 10 appear to be defect-free in the uniform lighting image. Circled areas 200, 202, 204, and 212 appear to be defects in the uniform lighting image of FIG. 12. The image of the defects and apparent defects is "flat", i.e, two dimensional.

FIG. 13 is an image of the same defects as shown in FIG. 11 utilizing a dual-level out-of-focus light source of the preferred embodiment, wherein the depth-of-field DOF of the camera is at a minimum setting, i.e., the lens aperture is open wide at an f-stop of 2.8. The apparent defect-free areas 206, 208, 210 and 214 of FIG. 12 reveal defects with the dual-level out-of focus light source applied to the web 10. In addition, defects 200 and 202 are accentuated, and appear three-dimensional in the image. Apparent defects 204 and 212 continue to appear in the image, however, the image of these apparent defects do not consist of bright and dark areas. Thus, it is likely that apparent defects 204 and 212 are dust particles on the surface of the web 10 since dust particles absorb/block light. The texture of the web material 10 is not prominent in the image of FIG. 13.

Sensitivity of the camera 14, that is, the level of detail in the image produced by the system of the preferred embodiment is controlled by the aperture of the lens on camera 14. As the aperture closes, the depth of field increases, and the pixel-size area of light rays 38 that are detected by the camera 14 decreases in size as it comes into focus. The resulting image of the web surface 10 reveals more pronounced deviations of refracted light on the web surface 10, and the texture of the web material becomes prominent in the image. As discussed with reference to FIG. 10, as the f-stop increases, the amount of light entering the lens decreases, and the gain of the camera 14 must be increased accordingly. The size of defects that a user wishes to detect utilizing the defect inspection system 2 of the present invention is dependent upon the camera depth of field.

FIG. 14 is an image of the same defects as shown in FIG. 11 utilizing a dual level out-of-focus light source of the preferred embodiment, wherein the depth-of-field of the camera is at a second setting. Specifically, the lens aperture is at an f-stop of 8. At this setting, apparent defects 204 and 210 no longer appear in the image, confirming that these areas may have contained surface dust. The defects 200, 202, 206, 208, 210 and 214 are more prominent in the image. Defect 200 is a crease on the surface of the web 10. Assuming that the defect inspection system 2 is configured as shown in FIGS. 8–11, defects 202, 206 and 214 are bumps on the web material 10, and defects 208 and 210 are indents in the web material 10. The depth of field utilized to produce this image provides more detail of the surface features of the web material 10.

FIG. 15 is an image of the same defects as shown in FIG. 11 utilizing a dual level out-of-focus dual light source of the preferred embodiment, wherein the depth-of-field of the camera is at a maximum setting, that is, the lens aperture is at an f-stop of 16. As can be seen in the image of FIG. 15, the detail of the web surface 10 is prominent, and the defects, in particular the smaller concave defects 208 and 210, are indistinguishable from the web surface 10 features. The ideal depth-of-field for this particular web material 10 appears to be in the range of the depth-of-field utilized to produce the images of either FIG. 13 or 14. However, as discussed above, it may be desirable in specific applications of the system 2, to detect minute defects.

Although a preferred embodiment of the invention has been described above by way of example only, it will be understood by those skilled in the field that modifications may be made to the disclosed embodiments of the defect detection system utilizing a dual level out-of-focus light source without departing from the scope of the invention, which is defined by the appended claims.

The Invention claimed is:

1. A system for inspecting a material, the system comprising:
   at least one dual level light source for illuminating the material, the at least one dual level light source comprising:
      at least one light emitting element for emitting light;
      a light diffuser covering the emitted light of the at least one light emitting element; and
      an opaque member having at least one straight edge placed over a portion of the light diffuser;
      the opaque member and light diffuser producing a light source surface having a bright portion and a dark portion; and
   at least one line scan camera aligning a single row of pixels so that the light source surface is detected on the row of pixels;
   wherein each pixel of the row of pixels has a no-defect brightness level when the each pixel produces a pixel image of a portion of the material having no defects.

2. The system as in claim 1, wherein a depth of field of the at least one line scan camera extends to include the material, but does not extend to include the at least one dual level light source.

3. The system as in claim 2, wherein a sensitivity of the system to defect a specific size of defect is adjustable by varying the depth of field of the at least one line scan camera.

4. The system as in claim 1, wherein the material is a web material moving in a first direction with respect to a first orientation of the bright portion and the dark portion of the light source surface.

5. The system as in claim 4, wherein the material is a non-opaque web material, and the at least one dual level light source provides back lighting of the non-opaque web material.

6. The system as in claim 4, wherein the material is an opaque web material, and the at least one dual level light source provides front lighting of the opaque web material.

7. The system as in claim 4, wherein the material comprises at least one convex defect, and wherein the at least one convex defect appears on an image of the plurality of images produced by the at least one line scan camera as a bright area followed by a dark area.

8. The system as in claim 4, wherein the material comprises at least one concave defect, and wherein the at least one concave defect appears on an image of the plurality of images produced by the at least one line scan camera as a dark area followed by a light area.

9. The system as in claim 1, wherein the at least one light emitting element comprises a plurality of light emitting diodes.

10. The system as in claim 1, wherein the no-defect brightness level of each pixel is half of a brightness level of the bright portion of the light source surface, and wherein a defect on the material is identifiable by comparing a brightness level of a plurality of pixels comprising an image of the defect to the no-defect brightness level.

11. A method for detecting defects on a material, the method comprising the steps of:
   applying a dual level light source to a material, the dual level light source having a light source surface comprising a dark portion and a bright portion with a transition line there between;
   focusing at least one line scan camera on the surface of the material;
   setting a depth of field of the at least one line scan camera to include the surface of the material, wherein the depth of field does not extend to include the dual level light source;
   centering a single row of pixels of the at least one line scan camera on the transition line when the row of pixels is focused on a portion of the material having no defect;
   establishing a no-defect brightness level of each pixel of the row of pixels focused on the portion of the material having no defect;
   moving the material in a direction with respect to the dark portion and the bright portion of the light source surface;
   producing a plurality of images comprising a plurality of consecutive line images produced by the single row of pixels; and
   analyzing the plurality of images to identify defect image areas of the plurality of images having a plurality of pixel brightness levels not equal to the no-defect brightness level.

12. The method as in claim 11, wherein the defect image areas of the plurality of images indicates a convex defect when the defect image area comprises a bright area adjacent a dark area.

13. The method as in claim 11, wherein the defect image area of the plurality of images indicates a convex defect when the defect image area comprises a dark area adjacent a bright area.

14. The method as in claim 11, wherein the depth of field is adjustable to define a defect detection sensitivity of the plurality of images.

15. The method as in claim 11, wherein the no-defect brightness level of each pixel comprises a no-defect range of brightness levels.

16. The method as in claim 11, further comprising the steps of:
   establishing a first range of brightness levels for identifying an upward sloping surface of a defect; and
   establishing second range of brightness levels for identifying a downward sloping surface of a defect.

17. A light source for illuminating a material under inspection, the light source comprising:
   at least one light emitting element for producing a plurality of light rays;
   at least one diffuser placed over the at least one light emitting element, the at least one diffuser for evenly spreading the plurality of light rays over a surface of the at least one diffuser;
   an opaque material fixed relative to the diffuser, and having a straight edge, the opaque material positioned on a first or a second side of the surface of the at least one diffuser to cover a portion of the surface of the at least one diffuser and to block a subset of the plurality of light rays;
   a housing for containing the at least one light emitting element, the at least one diffuser, and the opaque material, the housing having a opening aligned with the at least one diffuser;
   the opaque material and the at least one diffuser cooperating to produce a dual level light source having a light source surface comprising a bright portion and a dark portion with a transitional edge between the bright portion and the dark portion; and
   the straight edge being constructed with an edge sufficiently sharp so that the transitional edge is detectable by a single row of camera pixels.

18. The light source as in claim 17, wherein the bright portion and the dark portion of the light source surface have substantially equal surface areas.

19. The light source as in claim 17, wherein the at least one light emitting element comprises a plurality of light emitting diodes.

20. The light source as in claim 17, wherein the at least one diffuser emits a specific wavelength of light.

21. The system as in claim 1, wherein the opaque member and light diffuser are constructed to produce a light source surface having a bright portion and a dark portion with a transitional edge between the bright portion and the dark portion.

22. The system as in claim 21, wherein the row of pixels is aligned so that the transitional edge is projected onto the row of pixels.

23. The system as in claim 22, wherein the row of pixels is aligned so that the transitional edge is projected onto center of the row of pixels, so that in a no-defect condition each pixel is about half bright and about half dark.

24. A method for detecting defects on a material, the method comprising the steps of:
- generating a light pattern having sharp transition line from light to dark;
- positioning a single row of pixels of a line scan camera to detect the sharp transition line when the row of pixels is focused on a portion of the material having no defect;
- establishing a no-defect brightness level of each pixel of the single row of pixels focused on the portion of the material having no defect;
- moving the material;
- producing a plurality of images comprising a plurality of consecutive line images produced by the row of pixels; and
- detecting in the images that the position of the transition line has moved; and
- determining, responsive to the detecting step, the presence of a defect on the material.

* * * * *